United States Patent

Gherson et al.

[11] Patent Number: 6,022,747
[45] Date of Patent: Feb. 8, 2000

[54] BLOOD CLOT DETECTOR

[75] Inventors: Paul Gherson, Yorktown Heights; Robert William Eherts, Middletown; Theodore Pernicano, Yonkers, all of N.Y.

[73] Assignee: Bayer Corporation, Tarrytown, N.Y.

[21] Appl. No.: 09/113,647

[22] Filed: Jul. 10, 1998

[51] Int. Cl.[7] .................................................. G01N 27/416
[52] U.S. Cl. .............................................. 436/69; 436/148
[58] Field of Search ........................ 436/69, 148; 422/73; 73/64.41, 864.35

[56] References Cited

U.S. PATENT DOCUMENTS

| | | | |
|---|---|---|---|
| 3,754,444 | 8/1973 | Ure et al. ............................... | 73/423 A |
| 4,841,786 | 6/1989 | Schulz .................................... | 73/864.25 |
| 5,316,730 | 5/1994 | Blake et al. ............................. | 436/69 |
| 5,451,373 | 9/1995 | Lewis et al. ........................... | 422/82.13 |
| 5,503,036 | 4/1996 | Nguyen et al. ....................... | 73/864.34 |
| 5,540,081 | 7/1996 | Takeda et al. .............................. | 73/37 |
| 5,622,869 | 4/1997 | Lewis et al. ............................ | 436/148 |
| 5,814,275 | 9/1998 | Lewis et al. ............................... | 422/63 |

*Primary Examiner*—Philip R. Coe
*Attorney, Agent, or Firm*—Andrew L. Klawitter, Esq.; Rodman & Rodman

[57] ABSTRACT

A blood clot detector includes a pressure transducer on an aspiration line to provide output voltage data to a microprocessor corresponding to the vacuum level during aspiration. The microprocessor integrates the vacuum readings over time during the aspiration cycle to provide a pressure integral for each test sample aspiration. A pressure integral is determined for an unclotted aspiration and used as a reference for comparison with the pressure integrals of each test sample aspiration to determine whether a blood clot has interfered with the test sample aspiration. A valve is provided across an analytical line and an aspiration line to provide selective communication between the aspiration line and the analytical line or to prevent such communication. Communication between the aspiration line and the analytical line permits transfer of a test sample from the aspiration line to the analytical line if the test sample is considered acceptable for sample analysis. Acceptability of the test sample for analysis is based upon a predetermined difference between the reference pressure integral and each test sample pressure integral.

10 Claims, 3 Drawing Sheets

BLOOD CLOT DETECTOR

BACKGROUND OF THE INVENTION

This invention relates to an apparatus and method for detecting pipette tip obstructions and more particularly to a method and apparatus for detecting a blood clot obstruction at a pipette during aspiration of a blood sample for sample analysis.

In known automatic sampling systems, predetermined test sample volumes of blood or serum react with predetermined volumes of reagent to produce a measurable test result that is the basis for an analytical determination of blood characteristics. Known sampling systems usually include a pipette or sampling probe to aspirate test sample from a container such as a tube or cuvette.

If the pipette aspirates less than the predetermined test sample volume a flawed test result can occur since accurate test results require a predetermined test sample volume to react with a predetermined amount of reagent. As with many analytical processes a limited volumetric difference from the predetermined test sample volume may be tolerable for test purposes.

The volume of aspirated test sample can be predetermined when the aspiration occurs over a known time duration since the tip opening of the pipette is known and the aspiration flow rate of test sample into the pipette is known from the operational characteristics of the aspiration pump. Thus the aspiration of test sample is usually time controlled with the aspiration time corresponding to a predetermined volume of aspirated test sample.

It is also known that a blood sample in a container may contain a clot or clots and that such clots can close or obstruct the probe tip, impeding the aspiration. If movement of fluid into the probe is fully or partially blocked during a fixed aspiration time cycle a reduced volume of test sample will be aspirated. In some instances a clot or obstruction remains in the flow path of fluid directed into the probe and never clogs the probe. Nevertheless a flow path obstruction can also reduce the flow rate of fluid aspirated in a given time, thus preventing the aspirated test sample from reaching the predetermined volume in the preset aspiration time.

In other instances a clot or obstruction will enter and clog the probe, thereby reducing the flow rate of fluid being aspirated and preventing the predetermined volume of fluid from being aspirated in a preset aspiration time. Subsequent aspirations by the clogged probe will also be less than the expected predetermined sample volume. Since a limited volumetric difference from the predetermined test sample volume may be acceptable for test purposes, it is desirable to provide a system and method that distinguishes between acceptable aspiration volumes and unacceptable aspiration volumes.

Previous attempts to detect clot obstructed aspirations are generally based on a detection of pressure conditions during aspiration. For example, U.S. Pat. No. 5,503,036 to Nguyen et al shows an obstruction detection circuit with a pressure sensor to detect abnormal pressure conditions in a sample probe. The abnormal pressure conditions signify the presence of an obstruction.

U.S. Pat. No. 3,754,444 to Ure et al shows a medical sampling device that includes a clot detector that relies on a pressure increase in the fluid system to set off an alarm.

European Publication 0289946A2 to Itoh shows a pressure switch to detect pipette clogging. European Publication 0571100A1 to Tolonen shows a pressure transducer to detect pipette clogging. European Publication 0658769A1 to Takeda et al shows the use of pressure readings to detect a leakage condition in a pipette.

In most known blood clot detection systems the sample volume aspirated is relatively large, such as for example, approximately 200 microliters. Aspiration of a 200 microliter sample usually provides recognizable vacuum measurements in the aspiration line that can be detected by a pressure transducer or other pressure sensing device. A vacuum measurement that is made under normal unobstructed aspiration conditions can be used as a reference standard. Vacuum measurements are then made for each test sample aspiration and any deviation from the reference standard by a predetermined amount can indicate an obstructed aspiration. An appropriate warning signal can be generated in response to a deviant vacuum measurement to alert an operator that an obstructed probe condition has been detected.

Unless otherwise indicated the term "clot detection" as used hereinafter is intended to refer to the detection of an obstruction of an aspiration probe, caused by an internal clot in the probe, an external clot in the aspiration path outside the probe or any other obstruction that is internal or external of the probe that serves to reduce the amount or flow rate of fluid being aspirated in a predetermined time period.

Clot detection problems arise when an aspirated sample volume is relatively small such as for example approximately one to seven microliters. Aspiration of a one to seven microliter sample can be accomplished with a relatively small amount of vacuum in the range of one centimeter of water. However transducer measurement of a vacuum level of one centimeter of water is difficult to recognize because even a sensitive transducer has a noise level that is likely to obscure the detection or measurement of a vacuum level of one centimeter of water.

At vacuum levels in the range of one centimeter of water the transducer noise level also obscures the recognition of deviant vacuum levels that may indicate an obstructed aspiration. Thus far it is not feasible to rely on transducer based vacuum measurement for clot detection when aspirating samples of one to seven microliters.

It is therefore desirable to provide a method and apparatus for clot detection at an aspiration probe when the aspirated volumes are of the order of one to seven microliters and the vacuum levels are in the range of one centimeter of water.

OBJECTS AND SUMMARY OF THE INVENTION

Among the several objects of the invention may be noted the provision of a novel method of a blood clot detection during aspiration of a blood or serum sample, a novel method of blood clot detection during aspiration of one to seven microliters of blood or serum sample, a novel method of blood clot detection for aspiration systems that develop a vacuum in the range of one centimeter of water, a novel method of blood clot detection which is applicable to an analytical line that receives a sequence of spaced samples that are advanced in the analytical line by a continuing succession of samples, a novel method of distinguishing test samples that are acceptable for test purposes and test samples that are unacceptable for test purposes in a sample analysis system, a novel method of segregating an unacceptable aspirated test sample from a continuous flow of acceptable test samples, and a novel sampling system that provides selective isolation of an unacceptable test sample from an aggregation of acceptable test samples and selective joining of an acceptable test sample with other acceptable test samples.

Other objects and features of the invention will be in part apparent and in part pointed out hereinafter.

In accordance with the invention a sampling system includes an aspiration line having an aspiration pump in series with an aspiration probe. The sampling system further includes an analytical line having a reading station that is normally in communication with a stream pump. A valve having a vent outlet is disposed across the aspiration line and the analytical line and has a first valve position that prevents communication between the aspiration line and the analytical line. The first valve position also permits communication between the aspiration pump and the aspiration probe and also permits communication between the stream pump and the analytical line. The valve has a second valve position that prevents communication between the aspiration pump and the aspiration probe while permitting communication between the aspiration pump and the analytical line. The second valve position also enables the stream pump to vent through a valve vent.

A transducer is disposed on the aspiration line between the aspiration pump and the valve to detect pressure at the aspiration probe during aspiration of fluid. When a test sample is aspirated the valve is in the first valve position and the transducer provides output voltage readings at predetermined time intervals during the aspiration cycle that correspond to the vacuum level in the aspiration probe during aspiration. A microprocessor connected to the pressure transducer converts the voltage readings to pressure readings and integrates the pressure readings over time to provide a pressure integral for each aspiration.

A baseline or reference pressure integral is also developed for a known unclotted aspiration. The reference pressure integral is compared with each test sample aspiration pressure integral.

When the pressure integral for a test sample differs from the reference pressure integral by an amount greater than three standard deviations of the reference pressure integral it can be determined that the test sample aspiration was impeded by a blood clot and would not provide a reliable evaluation at the sampling system reading station.

The discrepant test sample aspiration is thus unacceptable for test purposes and is kept isolated from the analytical line when the valve is in the first valve position. The unacceptable test sample aspiration can also be removed from the aspiration line while the valve is in the first valve position. In addition the aspiration probe can be cleaned or replaced while the valve is in the first valve position since the first valve position isolates the analytical line from the aspiration line, and permits continuous flow of test samples in the analytical line by operation of the stream pump.

If the difference between the test sample aspiration pressure integral and the reference pressure integral is less than three standard deviations of the reference pressure integral the test sample is considered acceptable for test purposes and the valve is positioned in the second valve position.

With the valve in the second valve position, communication is provided between the aspiration line the analytical line and the aspiration pump. The aspiration pump is operated in a reverse direction to transfer the acceptable aspirated test sample from the aspiration line into the analytical line to join the other test samples in the analytical line as they move toward the reading station.

The invention also includes a method of detecting a blood clot or other obstruction while aspirating a test sample. The method requires aspirating a first predetermined volume of reference serum that is free of clots and obstructions across a probe opening of predetermined size and measuring the time duration of such reference serum aspiration. The vacuum level versus time of the reference serum aspiration is measured during the time duration of the reference serum aspiration. An integration is performed of the vacuum level versus time for a selected predetermined time duration during the measured time duration to establish a reference integral for the reference serum aspiration. A test serum is aspirated across the same probe opening of predetermined size during the measured time duration. The vacuum level of the test sample aspiration is measured versus time and an integration is performed of the vacuum level versus time for the test serum aspiration during the selected predetermined time duration to establish a test sample integral for the test serum aspiration.

The reference integral is used as a basis of comparison with the test sample integral to determine what difference if any exists between the test sample integral and the reference integral. If such difference exceeds a predetermined amount it is determined that a clot or other obstruction influenced the test serum aspiration and such aspiration is unacceptable for test purposes. The unacceptable test sample is prevented from entering an analytical line of a sample analysis system.

The invention also includes a method of segregating an unacceptable aspirated test sample from a continuous flow of acceptable test samples. The method includes providing an aspiration line with an aspiration probe, and an analytical line which conveys test samples to a reading station. An aspiration pump is provided in series with the aspiration probe on the aspiration line and a stream pump is provided in series with the reading station of the analytical line. A flow control device, such as a valve is provided across the aspiration line and the analytical line to optionally keep the flow in the analytical line separate from the flow of the aspiration line. The vacuum level of an aspirated test sample is measured to determine whether the aspirated test sample is acceptable or unacceptable. If the test sample is unacceptable the separate flow option is maintained to prevent the unacceptable test sample from entering the analytical line. If the test sample is acceptable, communication is established between the aspiration line and the analytical line to permit entry of the acceptable test sample into the analytical line.

The invention accordingly comprises the constructions and methods hereinafter described, the scope of the invention being indicated in the claims.

DESCRIPTION OF THE DRAWINGS

In the drawings.

Corresponding reference characters indicate corresponding parts throughout the several views of the drawings.

DETAILED DESCRIPTION OF THE INVENTION

Figure 1:
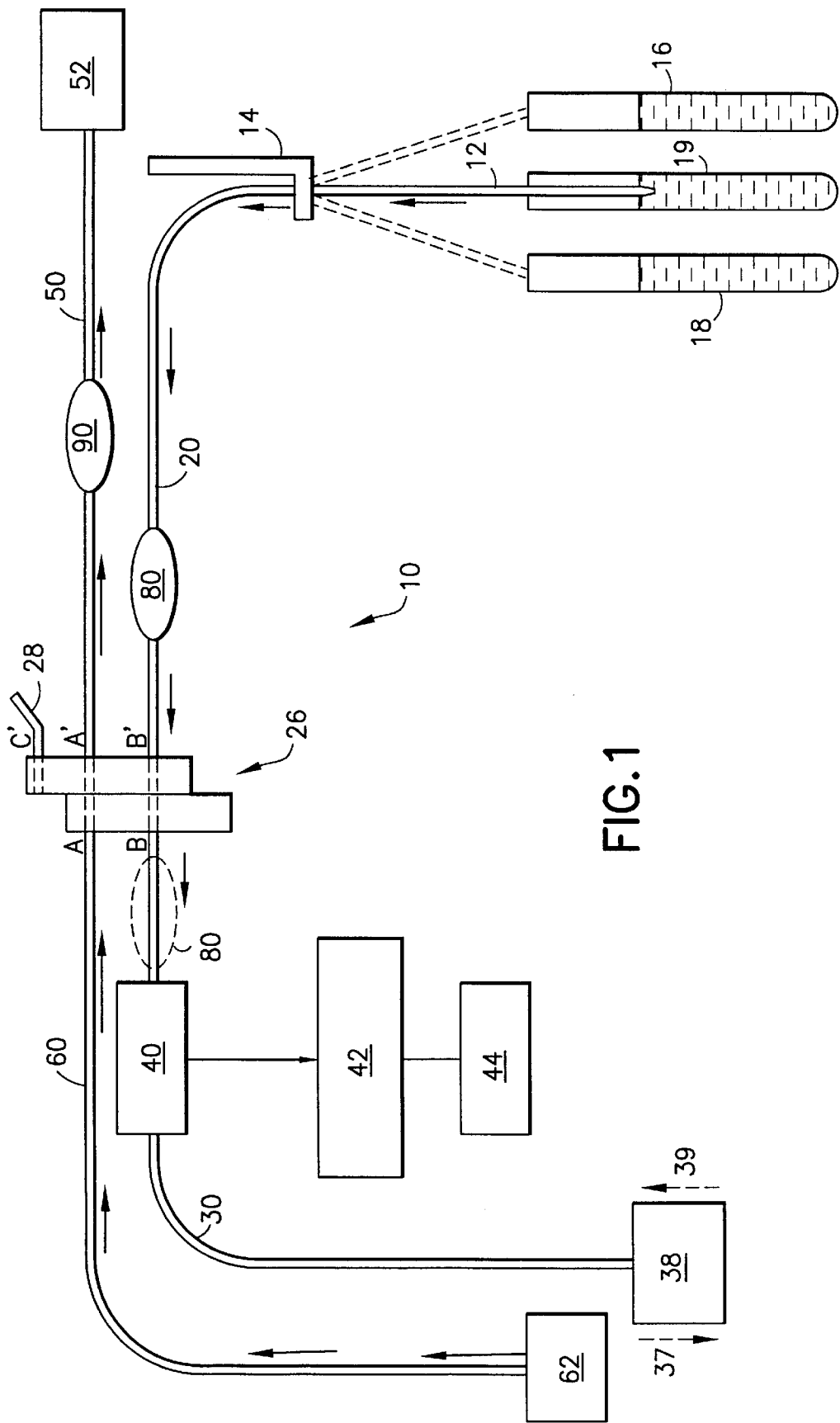
FIG. 1 is a simplified schematic view of an aspiration system with a blood clot detection system incorporating one embodiment of the present invention, the aspiration system being in an aspiration mode.
Figure 2:
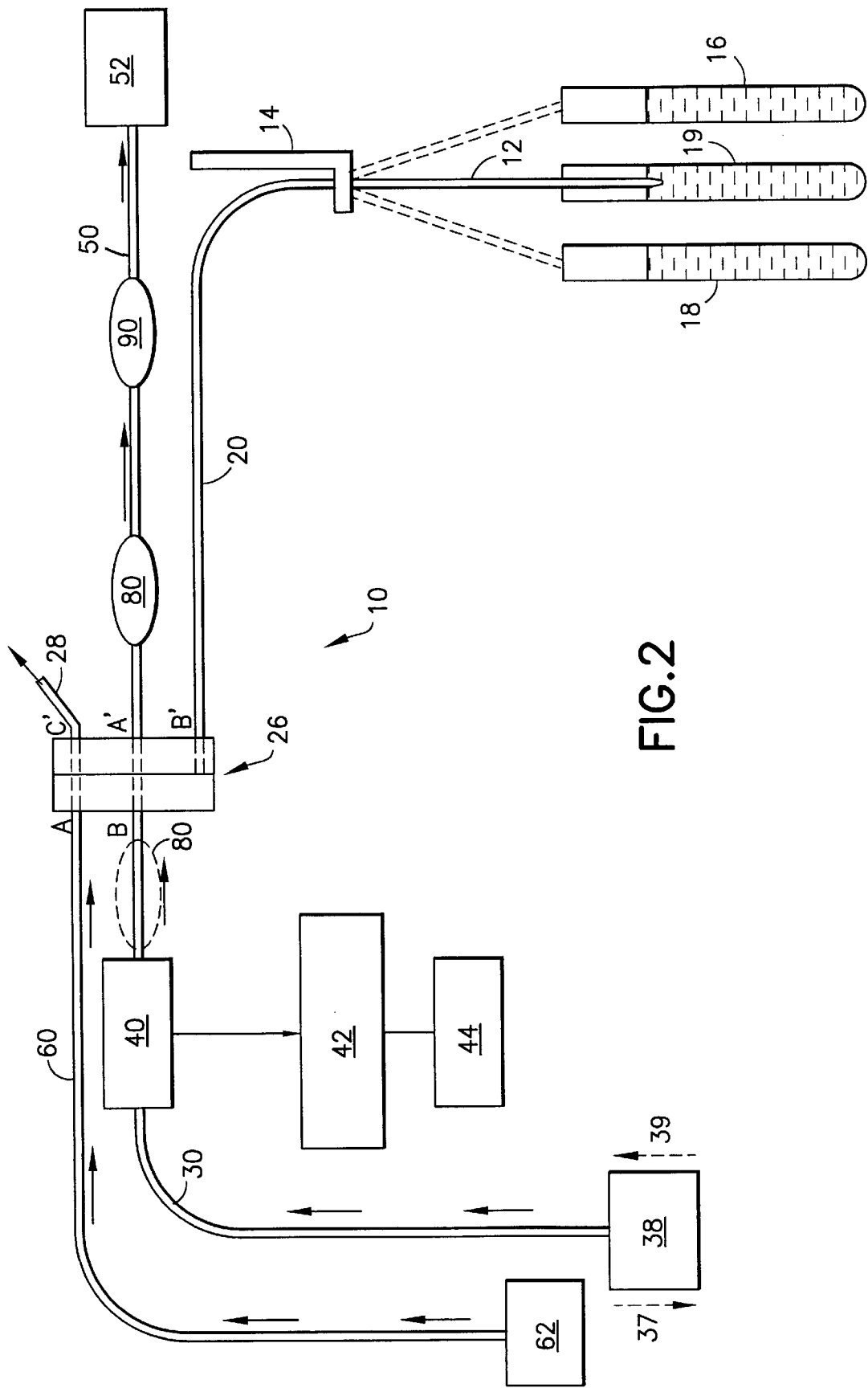
FIG. 2 is a view similar to FIG. 1 with the aspiration system in a non-aspiration mode.

Referring to FIGS. 1 and 2 of the drawings, a sampling system that incorporates one embodiment of the invention is generally indicated by the reference number 10.

The sampling system 10 includes an aspiration probe 12 supported by a suitable known moveable probe arm 14. The probe arm 14 positions the probe 12 to enter an oil reservoir 16, a reagent or buffer container 18 or a sample tube 19 for aspiration purposes. A conduit section 20, also referred to as an aspiration line, connects the aspiration probe 12 to a known valve 26 such as a shear valve with a vent 28. A conduit section 30, also referred as an aspiration line, is connected at one end to the valve 26 and is connected at an opposite end to an aspiration pump 38 such as a suitable known syringe pump.

A pressure transducer 40 is connected to the aspiration line 30 to measure the vacuum level in the aspiration line during aspiration of a test sample 80 by the probe 12. The test sample 80 is also referred to as a test capsule and includes test sample from the sample tube 19 and reagent from the container 18. All further discussion of test sample aspiration unless otherwise indicated relates solely to the aspiration of liquid from the sample tube 19. The transducer 40 is preferably a Sensym Model SX05DN, with a range of 0–5 psi, sold by Sensym Company of Milpitas, Calif. or comparable equivalent device. The transducer 40 is connected to a suitable known microprocessor 42 and the microprocessor is connected to a suitable known warning device 44 such as a visual or sound alarm.

The sampling system 10 further includes a conduit section 50, also referred to as an analytical line, having one end connected to the valve 26 and an opposite end is directed to a known sample analysis reading station 52. A conduit section 60, also referred to as a stream line, is connected at one end to the valve 26 and is connected at an opposite end to a suitable known stream pump 62 that provides an air stream.

During test sampling, the valve 26 is in a first valve position as shown in FIG. 1 to permit communication between the aspiration line 20 and the aspiration line 30. The first valve position of the valve 26 also permits communication between the analytical line 50 and the stream line 60 but prevents communication between the aspiration lines 20, 30 and the analytical and stream lines 50, 60. In the first valve position of the valve 26 there is also no communication between the valve vent 28 and the aspiration, analytical and stream lines 20, 30, 50, 60.

With the valve 26 in the first valve position of FIG. 1 the probe 12 initially enters the oil reservoir 16 to aspirate a predetermined amount of oil. The aspirated oil is drawn into the aspiration conduits 20 and 30 to the aspiration pump 38. The probe 12 is then positioned by the probe arm 14 to enter the reagent and buffer container 18 where a predetermined amount of reagent and buffer is aspirated. The probe 12 is further positioned by the probe arm 14 to enter the sample tube 19 to aspirate serum or test sample. Serum is aspirated for a predetermined time duration that corresponds to the withdrawal of a predetermined volume of test sample from the sample tube 19 into the probe 12.

Using a suitable known probe or pipette 12 and a suitable known syringe pump 38, a 1.1 microliter of test sample can be aspirated in a predetermined time such as approximately 300 milliseconds. Just before aspiration begins the pressure transducer 40 initially measures the pressure with the probe 12 immersed in the liquid of the sample tube 19. The initial transducer measurement represents drift in the transducer signal due to outside temperature and other ambient factors. The transducer 42 then measures the pressure during aspiration at predetermined time intervals such as approximately 5 millisecond intervals until the aspiration is completed. The transducer measurement is in the form of an output voltage V that corresponds to the aspiration vacuum. The output voltage of the transducer 40 at the predetermined time intervals are stored in the microprocessor 42.

Figure 3:
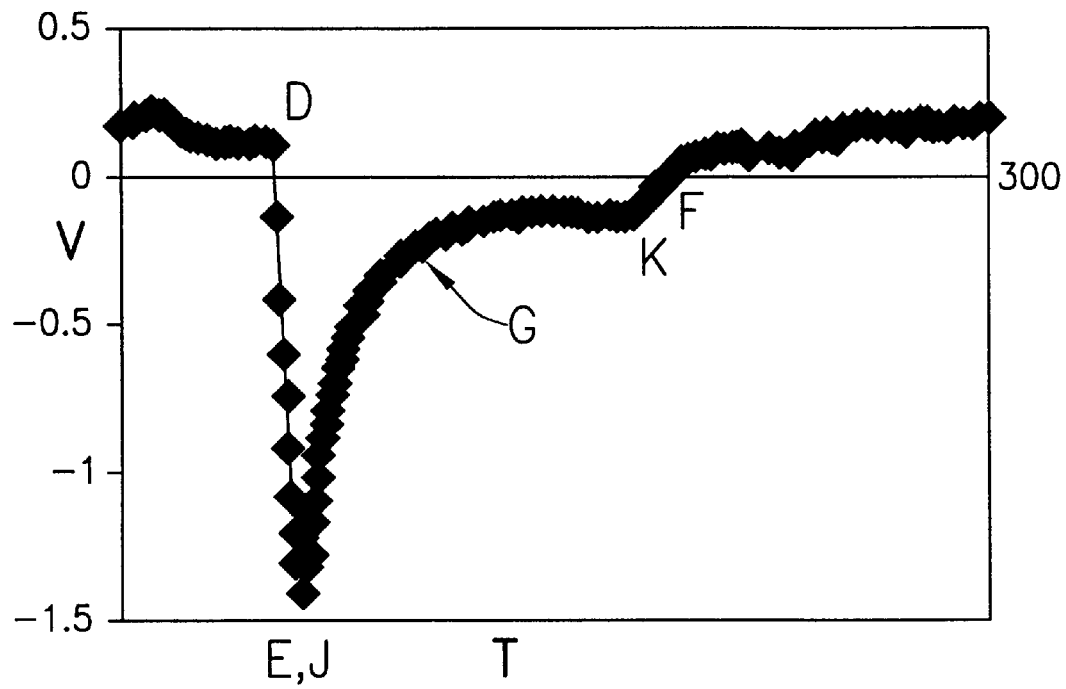
FIG. 3 is a vacuum trace for aspiration of unclotted plasma based on a plot of transducer voltage versus time; and, FIG. 4 is a vacuum trace made under similar conditions as in FIG. 3 for aspiration of clotted plasma.

Referring to FIG. 3 a vacuum trace of a 1.1 microliter aspiration of test serum that is free of blood clots or other obstructions is also referred to as a reference trace. The vacuum trace of FIG. 3 is based on output voltage of the transducer 40 plotted according to time T in milliseconds over an aspiration cycle of approximately 300 milliseconds. It can be seen from the reference trace of FIG. 3 that the aspiration cycle is characterized by an abrupt increase in vacuum, or decrease in pressure when fluid begins to enter the probe as indicated at points D to E on the trace. The vacuum gradually decreases from point E to point F as aspiration is completed resulting in a relatively smooth curve G that rises toward the zero axis of the vacuum trace.

Each test sample aspiration is conducted over the same predetermined time period using the same probe or pipette 12 and the same aspiration pump 38 that is used to produce the reference trace of FIG. 3. When a blood clot or other obstruction impedes the aspiration flow of test sample into the probe 12 it becomes imperative to detect such obstruction in order to ensure that reliable test results are obtained at the reading station 52 of the sample analysis system.

Figure 4:
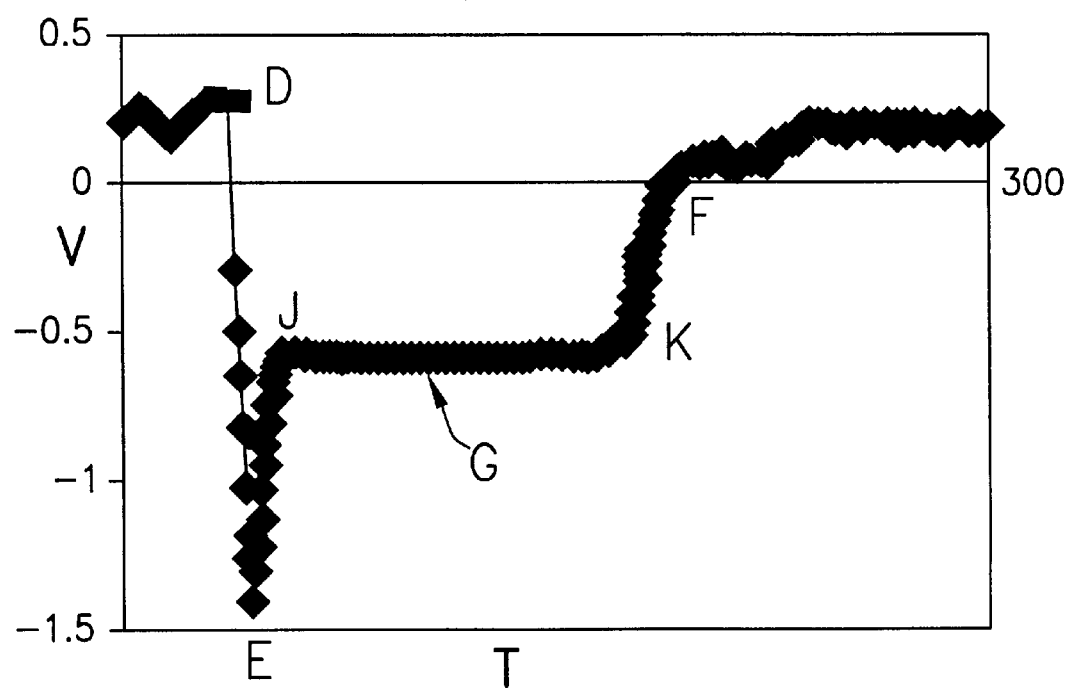

The vacuum trace for a clot impeded aspiration is shown in FIG. 4 and was made under the same conditions and with the same parameters used in the aspiration represented by the vacuum trace of FIG. 3.

It will be noted that the range of the transducer output voltage during each vacuum trace of FIGS. 3 and 4 is approximately the same except that there is a different duration of voltage or vacuum levels during the respective aspiration cycles. Generally, no single voltage or vacuum level distinguishes a clotted aspiration condition from an unclotted aspiration condition at the low levels of vacuum that are applied for a 1.1 microliter aspiration. The clot impeded vacuum trace of FIG. 4 is characterized by a prolonged, relatively high vacuum level between points J and K of the time cycle whereas the corresponding points J and K of the time cycle for the unclotted aspiration vacuum trace of FIG. 3 show a gradual decrease of vacuum level.

It can also be noted from the vacuum traces of FIGS. 3 and 4 that the area between the negative portion G of the vacuum trace and the zero axis in FIGS. 3 and 4 is noticeably different.

Applicants have found that by integrating the transducer output voltage levels versus time for select time intervals during each aspiration cycle, such as between E and F an area measurement is obtained that provides an easily recognizable quantitative distinction between the FIG. 3 vacuum trace for an unclotted aspiration and the FIG. 4 vacuum trace for a clotted aspiration. Integration of the transducer output voltage over time also serves a noise reduction function. By adding up the time intervals for which the vacuum is relatively strong with the time intervals for which the vacuum is relatively weak, the net result is proportional to the average vacuum. Therefore, an integration operation does not suffer the shortcomings of instantaneous voltage measurements that are obscured by the transducer noise that generally occurs at the relatively low vacuum levels used for aspirating 1.1 microliters of test sample.

In order to obtain the integral measurements that facilitate distinction between a clotted aspiration and an unclotted aspiration, the output voltage measurements of the pressure transducer are stored in the computer memory of the microprocessor 42 and are converted into pressure values using the known calibration curve of the pressure transducer 40. During or immediately after an aspiration time cycle is completed the microprocessor calculates a vacuum integral from the converted pressure values. The vacuum integral is hereinafter referred to as a pressure integral (PI).

The integration process is essentially a process wherein each vacuum value at 5 millisecond intervals, for example, is multiplied with the corresponding time interval over which the vacuum value is measured to obtain a multiplication result, and these multiplication results are added together for a given time duration to obtain the integral value. The integration is preferably made during the time intervals from points E to F in FIGS. 3 and 4 when the vacuum trace follows a path below the zero axis which provides the area of greatest distinction between the clotted and unclotted vacuum traces. This time interval from points E to F of the aspiration time cycle in FIGS. 3 and 4 is a shorter time duration than the time duration of the overall aspiration cycle.

The pressure integral (PI) for an aspiration is calculated using the following formula:

$$PI = \sum_{K=1}^{m}\left[p_k * dt - \frac{1}{n}\sum_{j=1}^{n}(p_j * dt)\right]$$

where, $p_k$=pressure value measured during the aspiration, m=number of measured pressure values $p_k$, $p_j$=pressure value measured with the probe immersed in liquid but before the aspiration starts, and n=number of measured pressure values $p_j$.

Once the pressure integral (PI) for a known unclotted test sample aspiration is calculated using the pressure integral formula, such integral can be used as a reference integral (PI ref). The mean value and standard deviation of such reference integral can be determined using known mathematical procedures. A pressure integral for the test sample assays (PI test) is then provided by the microprocessor 42 for each test sample aspiration.

The microprocessor 42 can be programmed using suitable known programming techniques to determine the difference between each test sample pressure integral and the reference pressure integral (PI test–PI ref). It has been found that when the pressure integral difference (PI dif) between the test sample pressure integral and the reference pressure integral is greater than three standard deviations of the reference integral, as where PI dif>3 SD or PI test–PI ref>3 SD the aspirated test sample will produce flawed test results. A test sample aspiration that is characterized by a PI dif>3 SD is thus unacceptable and when detected should be prevented from passing into the analytical line 50 to the reading station 52. When PI dif>3 SD the microprocessor 42 activates the alarm 44 in any suitable known manner to provide a visual or sound signal Reference pressure integrals also referred to as reference integrals can be obtained for selected aspiration volumes such as 1 microliter, 2 microliters, 3 microliters and so on. Using known mathematical techniques the reference integrals can be used to form a calibration curve for various selected aspiration volumes in a range, for example, of 1 to 7 microliters. The calibration curve can then permit interpolation or extrapolation of reference integral values for aspiration volumes that are in between or beyond the aspiration volumes actually used to form the basis for specific reference integrals.

The sampling system shown schematically in FIGS. 1 and 2 employs continuous flow capsule chemistry technology of the type shown in U.S. Pat. No. 5,268,147, the disclosure of which is hereby incorporated by reference in this specification. As previously noted the term test capsule is used to refer to a test sample and reagent that are sequentially aspirated by a probe and form a combined unit in an aspiration line. The terms test capsule and aspirated test sample are used interchangeably herein.

In known continuous flow capsule chemistry technology, a stream of segregated test capsules is fed continuously in an analytical line to a reading station. As new test capsules enter the analytical line, the stream of segregated capsules continuously advances toward the reading station so that each test capsule can be individually read or analyzed. Thus the advancement of test capsules toward the reading station is based on a continuous addition of new test capsules to the analytical line.

If the addition of new test capsules to the analytical line is suspended, the test capsules already in the analytical line are immobilized. When a test capsule is immobile the test results for such test capsules can be lost while the test capsules remain stationary in the analytical line because a reaction continues to occur between the test sample and the reagent that are combined at a predetermined time after aspiration begins. The test sample reaction should thus be read at the reading station within a predetermined time after the test sample has been aspirated.

In known sampling systems when an aspiration probe is clogged or the aspiration of the test sample is obstructed the discrepant sample can be removed from the aspiration line, the probe can be cleaned or replaced and the aspiration repeated. Such remedial operations usually hold up the continuous flow of test samples or test capsules in the analytical line. As previously noted any cessation of test capsule movement in an analytical line places the test results at risk of loss.

In the present sampling system if an aspirated sample in the aspiration line was impeded by a clot and is unacceptable for analysis, the stream of test capsules in the analytical line can still be continuously advanced to a reading station while the unacceptable test sample is removed from the system and while the probe is cleaned or replaced.

Referring to FIG. 1 the test sample 80 in the aspiration line 20 is subject to pressure measurement by the pressure transducer 40 during aspiration of the test sample 80 into the probe 12. If the difference between the pressure integral of the test sample 80 (PI test) and the reference integral (PI ref) is greater than three standard deviations, then the test sample 80 is unacceptable for analysis and should not be permitted to enter the analytical line 80. The test sample 80 should thus be removed from the aspiration line 20 or 30 and the probe 12 should be examined to determine whether a cleaning or replacement is warranted.

When the valve 26 is in the valve position of FIG. 1 such removal of an unacceptable test sample as well as the cleaning or replacement of the probe 12 can be accomplished without interfering with the continuous flow of test capsules in the analytical line 50. The valve 26 as positioned in FIG. 1 isolates the aspiration line 20, 30 from the analytical line 50, 60. Such isolation enables the stream pump 62 to provide an air stream to the analytical lines 60 and 50, to effect movement of test samples such as 90 in the analytical line 50 toward the reading station 52.

Stream pump movement of the test sample 90 in the analytical line 50 is accomplished even when remedial operations are being performed at the aspiration lines 20 or 30 to remove an unacceptable sample 80 and/or replace or clean the probe 12 and the analytical line 20. Thus whenever a sample probe 12 becomes incapacitated by clogging the probe 12 can be easily cleaned or replaced without stopping the progression of test samples such as 90 in the analytical line 50.

If the difference between the pressure integral for the test sample 80 (PI test) and the reference integral (PI ref) is less than three standard deviations, the test sample 80 can be transferred to the analytical line 50 for movement to the reading station 52. Such transfer is accomplished by first drawing the test sample 80 (shown dotted) to a position beyond valve 26 in the aspiration line 30. The valve 26 is then placed in the valve position of FIG. 2 to enable the aspiration line 30 to communicate with the analytical line 50 and to vent the stream pump 62 through the valve vent 28.

With the valve 26 in the valve position of FIG. 2 the aspiration pump 30 is operated in a direction indicated by the arrow 39. The test sample 80 and a predetermined amount of previously aspirated oil from the container 16 are thus caused to move from the aspiration line 30 to the analytical line 50. The transferred oil is used to separate consecutive test samples in the analytical line 50 in accordance with known sampling system techniques disclosed in U.S. Pat. No. 5,268,147. The test sample 80 thus joins the continuous stream of test samples such as 90 in the analytical line 50 that are moving toward the reading station 52.

After the test sample 80 has been transferred to the analytical line 50 the valve 26 is repositioned to the FIG. 1 valve position to prepare the sampling system 10 for aspiration of another test sample into the probe 12 in a manner similar to that previously described.

The valve 26 is thus positionable to maintain an aspirated test sample in the aspiration line 20, 30 in isolation from the analytical line 50, and stream line 60 (FIG. 1) and further positionable to permit transfer of an aspirated test sample from the aspiration line 30 to the analytical line 50.

Some advantages of the invention evident from the foregoing description include a method of detecting a blood clot or other obstruction while aspirating a test sample at relatively low vacuum levels such as 1 centimeter of water. Another advantage is a method of furnishing a recognizable distinction between an acceptable test sample and an unacceptable test sample whose aspiration was influenced by a blood clot. A further advantage is the use of pressure integrals as a basis of comparison between the vacuum characteristics of an acceptable test sample and an unacceptable test sample. The pressure integral serves as a noise reduction function that enables transducer output voltage at low level vacuum measurements to be formatted in a manner that permits distinction between the vacuum trace of an acceptable test sample and the vacuum trace of an unacceptable test sample influenced by a blood clot or other obstruction. Still another advantage is the provision of a sampling system wherein an aspiration line and an analytical line can be selectively maintained in isolation from each other when such isolation is desired and communicated with each other when such communication is desired. Selective communication between the aspiration line and the analytical line ensures a continuous flow of samples in an analytical line even when remediation procedures are being performed at the aspiration line.

In view of the above it will be seen that the several objects of the invention are achieved and other advantageous results obtained. As various changes can be made in the above constructions and methods without departing from the scope of the invention it is intended that all matter contained in the above description or shown in the accompanying drawings shall be interpreted as illustrative and not in a limiting sense.

What is claimed is:

1. A method of detecting a blood clot or other obstruction while aspirating a sample of serum for sample analysis comprising, (a) aspirating a first predetermined volume of reference serum that is free of clots and obstructions across a probe opening of predetermined size and measuring the time duration of such reference serum aspiration, (b) measuring vacuum level versus time of the reference serum aspiration during the measured time duration of the reference serum aspiration, (c) integrating the vacuum level versus time of the reference serum aspiration for a selected predetermined time duration during the measured time duration to establish a reference pressure integral for the reference serum aspiration, (d) aspirating test serum across the probe opening of predetermined size during the measured time duration, (e) measuring vacuum level versus time for the test serum aspiration and integrating the vacuum level versus time of the test serum aspiration during the selected predetermined time duration to establish a test serum pressure integral for the test serum aspiration, (f) using the reference pressure integral as a basis of comparison with the test serum pressure integral to determine whether there is a difference between the test serum pressure integral and the reference pressure integral, (g) calculating the difference between the reference pressure integral and the test serum pressure integral, and (h) using a predetermined difference between the reference pressure integral and the test serum pressure integral to indicate the presence of a clot or other obstruction.

2. The method of detecting a blood clot or other obstruction as claimed in claim 1, wherein the reference pressure integral is obtained by integrating the vacuum level of the reference pressure integral during the predetermined time duration and the test serum pressure integral is obtained by integrating the vacuum level of the test serum pressure integral during the predetermined time duration.

3. The method of detecting a blood clot or other obstruction as claimed in claim 1 wherein the predetermined difference between the reference pressure integral and the test serum pressure integral that is used to indicate the presence of a blood clot or other obstruction is an amount larger than one standard deviation of the reference pressure integral.

4. The method of detecting a blood clot or other obstruction as claimed in claim 1 wherein the predetermined difference between the reference pressure integral and the test serum pressure integral that is used to indicate the presence of a blood clot or other obstruction is any amount larger than three standard deviations of the reference pressure integral.

5. The method of detecting a blood clot or other obstruction as claimed in claim 1 wherein the vacuum level of the reference serum aspiration is measured at predetermined time intervals during the measured time duration.

6. The method of detecting a blood clot or other obstruction as claimed in claim 5 wherein the vacuum level of the test serum aspiration is measured at substantially the same predetermined time intervals as the vacuum level measurement for the test serum aspiration.

7. The method of detecting a blood clot or other obstruction as claimed in claim 6 wherein the reference pressure integral is obtained by multiplying each of the predetermined time intervals during the measured time duration of the reference serum aspiration by respective said vacuum levels measured during said predetermined time intervals and adding each said multiplication for the reference serum aspiration and the test serum pressure integral is obtained by multiplying each of the predetermined time intervals during the measured time duration of the test serum aspiration by respective said vacuum levels measured during the predetermined time intervals and adding each said multiplication for the test serum aspiration.

8. The method of detecting a blood clot or other obstruction as claimed in claim 6 wherein a pressure integral (PI) for the reference serum aspiration and a pressure integral (PI) for the test serum aspiration are each calculated in accordance with the formula:

$$PI = \sum_{k=1}^{m} \left[ p_k * dt - \frac{1}{n} \sum_{j=1}^{n} (p_j * dt) \right]$$

where, $p_k$=is a series of consecutive pressure values $p_1$, $p_2$, ... through $p_m$ measured during the aspiration, k refers to which of the pressure values $p_1$, $p_2$, ... through $p_m$ is the initial pressure value, m=total number of measured pressure values $p_k$, $p_j$=is a series of consecutive pressure values $p_1$, $p_2$ through $p_n$ measured with the probe immersed in serum but before the aspiration starts, j=refers to which of the pressure values $p_1$, $p_2$, ... through $p_n$ is the initial pressure value, and n=total number of measured pressure values $p_j$.

9. The method of detecting a blood clot or other obstruction as claimed in claim 8 wherein a test serum aspiration is determined to be clotted when PI (test serum)–PI (reference serum) is greater than three standard deviations of the pressure integral for the reference serum aspiration.

10. The method of detecting a blood clot or other obstruction as claimed in claim 8 wherein the vacuum levels of the reference serum aspiration and the test serum aspiration are measured by a transducer and output voltages of the transducer corresponding to the reference serum vacuum levels and the test serum vacuum levels are transmitted to a microprocessor to integrate vacuum level versus time for the reference serum aspiration and the test serum aspiration to establish the reference integral and the test sample integral.

* * * * *